United States Patent
Belhe et al.

(10) Patent No.: US 10,159,699 B2
(45) Date of Patent: Dec. 25, 2018

(54) SYSTEM AND METHOD FOR AFFECTING INTESTINAL MICROBIAL FLORA

(71) Applicant: MetaModix, Inc., Plymouth, MN (US)

(72) Inventors: Kedar R. Belhe, Minnetonka, MN (US); Todd Stangenes, Minneapolis, MN (US)

(73) Assignee: METAMODIX, INC., Plymouth, MN (US)

( * ) Notice: Subject to any disclaimer, the term of this patent is extended or adjusted under 35 U.S.C. 154(b) by 89 days.

(21) Appl. No.: 14/156,209

(22) Filed: Jan. 15, 2014

(65) Prior Publication Data

US 2014/0200502 A1    Jul. 17, 2014

Related U.S. Application Data

(60) Provisional application No. 61/752,839, filed on Jan. 15, 2013.

(51) Int. Cl.
| | |
|---|---|
| *A61M 5/00* | (2006.01) |
| *A61K 35/741* | (2015.01) |
| *A61F 5/00* | (2006.01) |
| *A61F 2/04* | (2013.01) |

(52) U.S. Cl.
CPC .............. *A61K 35/741* (2013.01); *A61F 2/04* (2013.01); *A61F 5/0076* (2013.01); *A61F 2002/044* (2013.01); *A61F 2002/045* (2013.01)

(58) Field of Classification Search
CPC .................. A61F 5/0076; A61F 5/0079; A61F 2002/044; A61F 2002/045; A61F 2/004; A61K 35/741
See application file for complete search history.

(56) References Cited

U.S. PATENT DOCUMENTS

| | | | |
|---|---|---|---|
| 4,134,405 A | 1/1979 | Smit | |
| 4,204,530 A | 5/1980 | Finney | |
| 4,246,893 A | 1/1981 | Berson | |
| 4,314,405 A | 2/1982 | Park | |
| 4,315,509 A | 2/1982 | Smit | |
| 4,416,267 A | 11/1983 | Garren et al. | |
| 4,501,264 A | 2/1985 | Rockey | |
| 4,641,653 A | 2/1987 | Rockey | |
| 4,716,900 A | 1/1988 | Ravo et al. | |

(Continued)

FOREIGN PATENT DOCUMENTS

| | | |
|---|---|---|
| AU | 2006227471 B2 | 9/2006 |
| AU | 2014200766 B2 | 6/2015 |

(Continued)

OTHER PUBLICATIONS

Better Nutrition: Your guide to Natural Living, Bouncing Back (http://www.betternutrition.com/natural-surgery-recovery-antiobiotics-probiotics/, Sep. 2009, accessed Jun. 14, 2016.*

(Continued)

*Primary Examiner* — Ariana Zimbouski
(74) *Attorney, Agent, or Firm* — Faegre Baker Daniels LLP (57) ABSTRACT

Described is a system for affecting intestinal microbial flora. The system includes an intestinal sleeve that is implanted in a patient and bypasses a section of the intestine; and probiotics, prebiotics or pharmacologic therapy used in combination with the intestinal sleeve. Also described are related methods.

5 Claims, 11 Drawing Sheets

(56) References Cited

U.S. PATENT DOCUMENTS

| | | |
|---|---|---|
| 4,719,916 A | 1/1988 | Ravo |
| 4,763,653 A | 8/1988 | Rockey |
| 4,899,747 A | 2/1990 | Garren et al. |
| 4,905,693 A | 3/1990 | Ravo |
| 5,234,454 A | 8/1993 | Bangs |
| 5,246,456 A | 9/1993 | Wilkinson |
| 5,306,300 A | 4/1994 | Berry |
| 5,322,697 A | 6/1994 | Meyer |
| 5,423,872 A | 6/1995 | Cigaina |
| 5,474,563 A | 12/1995 | Myler et al. |
| 5,480,423 A | 1/1996 | Ravenscroft et al. |
| 5,749,921 A | 5/1998 | Lenker et al. |
| 5,753,253 A | 5/1998 | Meyer |
| 5,755,769 A | 5/1998 | Richard et al. |
| 5,820,584 A | 10/1998 | Crabb |
| 6,017,563 A | 1/2000 | Knight et al. |
| 6,224,627 B1 | 5/2001 | Armstrong et al. |
| 6,267,988 B1 | 7/2001 | Meyer |
| 6,368,617 B1 * | 4/2002 | Hastings .............. A61K 31/565 424/439 |
| 6,454,699 B1 | 9/2002 | Forsell |
| 6,540,789 B1 | 4/2003 | Silverman et al. |
| 6,558,400 B2 | 5/2003 | Deem et al. |
| 6,675,809 B2 | 1/2004 | Stack et al. |
| 6,676,674 B1 | 1/2004 | Dudai |
| 6,740,121 B2 | 5/2004 | Geitz |
| 6,755,869 B2 | 6/2004 | Geitz |
| 6,802,868 B2 | 10/2004 | Silverman et al. |
| 6,845,776 B2 | 1/2005 | Stack et al. |
| 6,946,002 B2 | 9/2005 | Geitz |
| 6,994,095 B2 | 2/2006 | Burnett |
| 7,025,791 B2 | 4/2006 | Levine et al. |
| 7,037,343 B2 | 5/2006 | Imran |
| 7,037,344 B2 | 5/2006 | Kagan et al. |
| 7,044,979 B2 | 5/2006 | Silverman et al. |
| 7,090,699 B2 | 8/2006 | Geitz |
| 7,111,627 B2 | 9/2006 | Stack et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,163,554 B2 | 1/2007 | Williams et al. |
| 7,175,638 B2 | 2/2007 | Gannoe et al. |
| 7,175,669 B2 | 2/2007 | Geitz |
| 7,211,094 B2 | 5/2007 | Gannoe et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,261,725 B2 | 8/2007 | Binmoeller |
| 7,267,694 B2 | 9/2007 | Levine et al. |
| 7,288,099 B2 | 10/2007 | Deem et al. |
| 7,288,101 B2 | 10/2007 | Deem et al. |
| 7,291,160 B2 | 11/2007 | DeLegge |
| 7,306,614 B2 | 12/2007 | Weller et al. |
| 7,314,489 B2 | 1/2008 | McKenna et al. |
| 7,316,716 B2 | 1/2008 | Egan |
| 7,329,285 B2 | 2/2008 | Levine et al. |
| 7,335,210 B2 | 2/2008 | Smit |
| 7,347,875 B2 | 3/2008 | Levine et al. |
| 7,354,454 B2 | 4/2008 | Stack et al. |
| 7,364,542 B2 | 4/2008 | Jambor et al. |
| 7,364,591 B2 | 4/2008 | Silverman et al. |
| 7,367,937 B2 | 5/2008 | Jambor et al. |
| 7,431,725 B2 | 10/2008 | Stack et al. |
| 7,476,256 B2 | 1/2009 | Meade et al. |
| 7,503,922 B2 | 3/2009 | Deem et al. |
| 7,507,218 B2 | 3/2009 | Aliski et al. |
| 7,510,559 B2 | 3/2009 | Deem et al. |
| 7,513,914 B2 | 4/2009 | Schurr |
| 7,569,056 B2 | 8/2009 | Cragg et al. |
| 7,601,178 B2 | 10/2009 | Imran |
| 7,608,114 B2 | 10/2009 | Levine et al. |
| 7,608,578 B2 | 10/2009 | Miller |
| 7,618,435 B2 | 11/2009 | Opolski |
| 7,628,821 B2 | 12/2009 | Stack et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,815,589 B2 | 10/2010 | Levine et al. |
| 7,837,643 B2 | 11/2010 | Levine et al. |
| 7,837,669 B2 | 11/2010 | Dann et al. |
| 7,935,073 B2 | 5/2011 | Levine et al. |
| 7,976,488 B2 | 7/2011 | Levine et al. |
| 7,981,163 B2 | 7/2011 | Levine et al. |
| 8,105,392 B2 | 1/2012 | Durgin |
| 8,114,045 B2 | 2/2012 | Surti |
| 8,182,441 B2 | 5/2012 | Swain et al. |
| 8,211,186 B2 | 7/2012 | Belhe et al. |
| 8,282,598 B2 | 10/2012 | Belhe et al. |
| 8,579,849 B2 | 11/2013 | Grau et al. |
| 8,702,641 B2 | 4/2014 | Belhe et al. |
| 8,702,642 B2 | 4/2014 | Belhe et al. |
| 8,882,698 B2 | 11/2014 | Levine et al. |
| 9,044,300 B2 | 6/2015 | Belhe et al. |
| 9,173,760 B2 | 11/2015 | Belhe et al. |
| 2002/0183768 A1 | 12/2002 | Deem et al. |
| 2002/0188354 A1 | 12/2002 | Peghini |
| 2003/0040804 A1 | 2/2003 | Stack et al. |
| 2003/0040808 A1 | 2/2003 | Stack et al. |
| 2003/0060894 A1 | 3/2003 | Dua et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0158601 A1 | 8/2003 | Silverman et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2004/0019388 A1 | 1/2004 | Starkebaum |
| 2004/0024386 A1 | 2/2004 | Deem et al. |
| 2004/0039452 A1 | 2/2004 | Bessler |
| 2004/0088022 A1 | 5/2004 | Chen |
| 2004/0092892 A1 | 5/2004 | Kagan et al. |
| 2004/0093091 A1 | 5/2004 | Gannoe et al. |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122526 A1 | 6/2004 | Imran |
| 2004/0133147 A1 | 7/2004 | Woo |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0199262 A1 | 10/2004 | Dua et al. |
| 2004/0204768 A1 | 10/2004 | Geitz |
| 2004/0220682 A1 | 11/2004 | Levine et al. |
| 2004/0249362 A1 | 12/2004 | Levine et al. |
| 2005/0004681 A1 | 1/2005 | Stack et al. |
| 2005/0022827 A1 | 2/2005 | Woo et al. |
| 2005/0033226 A1 | 2/2005 | Kim |
| 2005/0033331 A1 | 2/2005 | Burnett et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0070934 A1 | 3/2005 | Tanaka et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080444 A1 | 4/2005 | Kraemer et al. |
| 2005/0080480 A1 | 4/2005 | Bolea et al. |
| 2005/0080491 A1 | 4/2005 | Levine et al. |

(56) References Cited

U.S. PATENT DOCUMENTS

| | | |
|---|---|---|
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149200 A1 | 7/2005 | Silverman et al. |
| 2005/0177181 A1 | 8/2005 | Kagan et al. |
| 2005/0183730 A1 | 8/2005 | Byrum |
| 2005/0192614 A1 | 9/2005 | Binmoeller |
| 2005/0197714 A1 | 9/2005 | Sayet |
| 2005/0228413 A1 | 10/2005 | Binmoeller et al. |
| 2005/0228504 A1 | 10/2005 | Demarais |
| 2005/0240279 A1 | 10/2005 | Kagan et al. |
| 2005/0246037 A1 | 11/2005 | Starkebaum |
| 2005/0247320 A1 | 11/2005 | Stack et al. |
| 2005/0250980 A1 | 11/2005 | Swanstrom et al. |
| 2005/0251157 A1 | 11/2005 | Saadat et al. |
| 2005/0251206 A1 | 11/2005 | Maahs et al. |
| 2005/0256587 A1 | 11/2005 | Egan |
| 2005/0267499 A1 | 12/2005 | Stack et al. |
| 2005/0273060 A1 | 12/2005 | Levy et al. |
| 2005/0277963 A1 | 12/2005 | Fields |
| 2005/0283107 A1 | 12/2005 | Kalanovic et al. |
| 2005/0288555 A1 | 12/2005 | Binmoeller |
| 2006/0009858 A1 | 1/2006 | Levine et al. |
| 2006/0020247 A1 | 1/2006 | Kagan et al. |
| 2006/0020277 A1 | 1/2006 | Gostout et al. |
| 2006/0030949 A1 | 2/2006 | Geitz |
| 2006/0036267 A1 | 2/2006 | Saadat et al. |
| 2006/0064120 A1 | 3/2006 | Levine et al. |
| 2006/0155310 A1 | 7/2006 | Binmoeller |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0178691 A1 | 8/2006 | Binmoeller |
| 2006/0206063 A1 | 9/2006 | Kagan et al. |
| 2006/0206064 A1 | 9/2006 | Kagan et al. |
| 2006/0249165 A1 | 11/2006 | Silverman et al. |
| 2006/0258906 A1 | 11/2006 | Binmoeller |
| 2006/0265082 A1 | 11/2006 | Meade et al. |
| 2006/0282087 A1 | 12/2006 | Binmoeller |
| 2006/0293742 A1 | 12/2006 | Dann et al. |
| 2007/0004963 A1 | 1/2007 | Benchetrit |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0021761 A1 | 1/2007 | Phillips |
| 2007/0027548 A1 | 2/2007 | Levine et al. |
| 2007/0032702 A1 | 2/2007 | Ortiz |
| 2007/0032879 A1 | 2/2007 | Levine et al. |
| 2007/0038308 A1 | 2/2007 | Geitz |
| 2007/0060932 A1 | 3/2007 | Stack et al. |
| 2007/0078302 A1 | 4/2007 | Ortiz et al. |
| 2007/0083271 A1 | 4/2007 | Levine et al. |
| 2007/0100367 A1 | 5/2007 | Quijano et al. |
| 2007/0118158 A1 | 5/2007 | Deem et al. |
| 2007/0118159 A1 | 5/2007 | Deem et al. |
| 2007/0135825 A1 | 6/2007 | Binmoeller |
| 2007/0167963 A1 | 7/2007 | Deem et al. |
| 2007/0198074 A1 | 8/2007 | Dann et al. |
| 2007/0203517 A1 | 8/2007 | Williams et al. |
| 2007/0213740 A1 | 9/2007 | Deem et al. |
| 2007/0213748 A1 | 9/2007 | Deem et al. |
| 2007/0213751 A1 | 9/2007 | Scirica et al. |
| 2007/0213837 A1 | 9/2007 | Ferreri et al. |
| 2007/0219570 A1 | 9/2007 | Deem et al. |
| 2007/0239284 A1 | 10/2007 | Skerven et al. |
| 2007/0250083 A1 | 10/2007 | Deem et al. |
| 2007/0250132 A1 | 10/2007 | Burnett |
| 2007/0265709 A1 | 11/2007 | Rajan et al. |
| 2007/0276432 A1 | 11/2007 | Stack et al. |
| 2007/0282349 A1 | 12/2007 | Deem et al. |
| 2007/0282418 A1 | 12/2007 | Weitzner |
| 2007/0282452 A1 | 12/2007 | Weitzner et al. |
| 2007/0282453 A1 | 12/2007 | Weitzner et al. |
| 2007/0282454 A1 | 12/2007 | Krueger et al. |
| 2007/0293885 A1 | 12/2007 | Binmoeller |
| 2008/0033574 A1 | 2/2008 | Bessler et al. |
| 2008/0045803 A1 | 2/2008 | Williams et al. |
| 2008/0065122 A1 | 3/2008 | Stack et al. |
| 2008/0065136 A1 | 3/2008 | Young |
| 2008/0071383 A1 | 3/2008 | Levine et al. |
| 2008/0086214 A1 | 4/2008 | Hardin et al. |
| 2008/0092910 A1 | 4/2008 | Brooks |
| 2008/0097466 A1 | 4/2008 | Levine et al. |
| 2008/0103604 A1 | 5/2008 | Levine et al. |
| 2008/0109086 A1 | 5/2008 | Voegele et al. |
| 2008/0109087 A1 | 5/2008 | Durgin |
| 2008/0140172 A1 | 6/2008 | Carpenter et al. |
| 2008/0161935 A1 | 7/2008 | Albrecht et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0167724 A1 | 7/2008 | Ruane et al. |
| 2008/0183238 A1 | 7/2008 | Chen |
| 2008/0195225 A1 | 8/2008 | Silverman et al. |
| 2008/0195226 A1 | 8/2008 | Williams et al. |
| 2008/0208135 A1 | 8/2008 | Annunziata |
| 2008/0208161 A1 | 8/2008 | Kaji et al. |
| 2008/0208224 A1 | 8/2008 | Surti et al. |
| 2008/0208239 A1 | 8/2008 | Annunziata |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0221597 A1 | 9/2008 | Wallace et al. |
| 2008/0221702 A1 | 9/2008 | Wallace et al. |
| 2008/0234834 A1 | 9/2008 | Meade et al. |
| 2008/0243151 A1 | 10/2008 | Binmoeller et al. |
| 2008/0249533 A1 | 10/2008 | Godin |
| 2008/0249566 A1 | 10/2008 | Harris et al. |
| 2008/0249635 A1 | 10/2008 | Weitzner et al. |
| 2008/0255476 A1 | 10/2008 | Boyajian et al. |
| 2008/0255587 A1 | 10/2008 | Cully et al. |
| 2008/0255594 A1 | 10/2008 | Cully et al. |
| 2008/0255678 A1* | 10/2008 | Cully ............... A61F 2/04 623/23.65 |
| 2008/0262529 A1 | 10/2008 | Jacques |
| 2008/0269715 A1 | 10/2008 | Faller et al. |
| 2008/0269797 A1 | 10/2008 | Stack et al. |
| 2008/0287969 A1 | 11/2008 | Tsonton et al. |
| 2008/0312559 A1 | 12/2008 | Santilli et al. |
| 2008/0319455 A1 | 12/2008 | Harris et al. |
| 2009/0005637 A1 | 1/2009 | Chin et al. |
| 2009/0012541 A1 | 1/2009 | Dahl et al. |
| 2009/0012542 A1 | 1/2009 | N'diaye et al. |
| 2009/0012544 A1 | 1/2009 | Thompson et al. |
| 2009/0012553 A1 | 1/2009 | Swain et al. |
| 2009/0076588 A1 | 3/2009 | Weber |
| 2009/0093767 A1 | 4/2009 | Kelleher |
| 2009/0093839 A1 | 4/2009 | Kelleher |
| 2009/0110664 A1* | 4/2009 | Moore ............... C12N 1/20 424/93.4 |
| 2009/0118749 A1 | 5/2009 | Shalon et al. |
| 2009/0125119 A1 | 5/2009 | Obermiller et al. |
| 2009/0138094 A1 | 5/2009 | Schurr |
| 2009/0149871 A9 | 6/2009 | Kagan et al. |
| 2009/0164028 A1 | 6/2009 | Chen |
| 2009/0177215 A1 | 7/2009 | Stack et al. |
| 2009/0182355 A1 | 7/2009 | Levine et al. |
| 2009/0187206 A1 | 7/2009 | Binmoeller et al. |
| 2009/0198210 A1 | 8/2009 | Burnett et al. |
| 2009/0216262 A1 | 8/2009 | Burnett et al. |
| 2009/0240105 A1 | 9/2009 | Smit et al. |
| 2009/0240340 A1 | 9/2009 | Levine et al. |
| 2009/0248171 A1 | 10/2009 | Levine et al. |
| 2009/0276055 A1 | 11/2009 | Harris et al. |
| 2009/0281379 A1 | 11/2009 | Binmoeller et al. |
| 2009/0299486 A1 | 12/2009 | Shohat et al. |
| 2009/0299487 A1 | 12/2009 | Stack et al. |

(56) References Cited

U.S. PATENT DOCUMENTS

| | | |
|---|---|---|
| 2009/0326433 A1 | 12/2009 | Albrecht et al. |
| 2009/0326675 A1 | 12/2009 | Albrecht et al. |
| 2010/0004755 A1 | 1/2010 | Imran |
| 2010/0016988 A1 | 1/2010 | Stack et al. |
| 2010/0030017 A1 | 2/2010 | Baker et al. |
| 2010/0135971 A1 | 6/2010 | Schiffrin |
| 2010/0256775 A1* | 10/2010 | Belhe .............. A61F 5/0076 623/23.65 |
| 2010/0305590 A1 | 12/2010 | Holmes et al. |
| 2011/0004320 A1* | 1/2011 | Priplata .............. A61F 2/04 623/23.65 |
| 2011/0009690 A1 | 1/2011 | Belhe et al. |
| 2011/0104327 A1* | 5/2011 | Kirejevas .............. A23K 40/30 426/2 |
| 2011/0106273 A1 | 5/2011 | Belhe et al. |
| 2012/0065571 A1 | 3/2012 | Thompson et al. |
| 2012/0109188 A1* | 5/2012 | Viola .............. A61B 17/064 606/213 |
| 2012/0184893 A1 | 7/2012 | Thompson et al. |
| 2012/0232460 A1* | 9/2012 | Raven .............. A61B 5/0031 604/9 |
| 2012/0253259 A1 | 10/2012 | Belhe et al. |
| 2012/0253260 A1 | 10/2012 | Belhe et al. |
| 2012/0302936 A1 | 11/2012 | Belhe et al. |
| 2013/0030351 A1 | 1/2013 | Belhe et al. |
| 2013/0324907 A1 | 12/2013 | Huntley et al. |
| 2014/0194806 A1 | 7/2014 | Belhe et al. |
| 2014/0309576 A1 | 10/2014 | Belhe et al. |
| 2014/0350694 A1 | 11/2014 | Behan |
| 2014/0379093 A1 | 12/2014 | Durgin |
| 2016/0089256 A1 | 3/2016 | Belhe et al. |
| 2016/0228276 A1 | 8/2016 | Thompson et al. |

FOREIGN PATENT DOCUMENTS

| | | |
|---|---|---|
| CN | 1575155 A | 2/2005 |
| CN | 1618411 A | 5/2005 |
| EP | 0137878 A1 | 4/1985 |
| EP | 1420730 A2 | 5/2004 |
| EP | 1492477 A1 | 1/2005 |
| EP | 1492478 A1 | 1/2005 |
| EP | 1555970 A1 | 7/2005 |
| EP | 1569582 A2 | 9/2005 |
| EP | 1585458 A1 | 10/2005 |
| EP | 1680054 A1 | 7/2006 |
| EP | 1708641 A1 | 10/2006 |
| EP | 1708655 A1 | 10/2006 |
| EP | 1709508 A2 | 10/2006 |
| EP | 1749482 A2 | 2/2007 |
| EP | 1750595 A2 | 2/2007 |
| EP | 1778069 A1 | 5/2007 |
| EP | 1786310 A2 | 5/2007 |
| EP | 1799145 A1 | 6/2007 |
| EP | 1817072 A2 | 8/2007 |
| EP | 1832250 A1 | 9/2007 |
| EP | 1850811 A1 | 11/2007 |
| EP | 1850812 A1 | 11/2007 |
| EP | 1881781 A2 | 1/2008 |
| EP | 1887995 A2 | 2/2008 |
| EP | 1895887 A2 | 3/2008 |
| EP | 1937164 A1 | 7/2008 |
| EP | 1992314 A1 | 11/2008 |
| EP | 1416861 B1 | 12/2008 |
| EP | 1749480 B1 | 12/2008 |
| EP | 2010270 A2 | 1/2009 |
| EP | 1610720 B1 | 2/2009 |
| EP | 2023828 A2 | 2/2009 |
| EP | 2026713 A2 | 2/2009 |
| EP | 2061397 A1 | 5/2009 |
| EP | 2066243 A1 | 6/2009 |
| EP | 2068719 A2 | 6/2009 |
| EP | 2080242 A2 | 7/2009 |
| EP | 1520528 B1 | 9/2009 |
| EP | 1610719 B1 | 1/2010 |
| EP | 1603488 B1 | 4/2010 |
| EP | 1585460 B1 | 5/2010 |
| EP | 1933721 B1 | 5/2010 |
| EP | 1768618 B1 | 4/2011 |
| EP | 1883370 B1 | 8/2011 |
| EP | 2945566 A1 | 11/2015 |
| JP | 2005500127 A | 1/2005 |
| JP | 2007513684 A | 5/2007 |
| JP | 2007513685 A1 | 5/2007 |
| WO | WO1998049943 A2 | 11/1998 |
| WO | WO2002096327 A2 | 12/2002 |
| WO | WO2003017882 A2 | 3/2003 |
| WO | WO2003086246 A1 | 10/2003 |
| WO | WO2003086247 A1 | 10/2003 |
| WO | WO2003094785 A1 | 11/2003 |
| WO | WO2004011085 A1 | 2/2004 |
| WO | WO2004017863 A2 | 3/2004 |
| WO | WO2004041133 A1 | 5/2004 |
| WO | WO2004064680 A1 | 8/2004 |
| WO | WO2004064685 A1 | 8/2004 |
| WO | WO2004087014 A2 | 10/2004 |
| WO | WO2004087233 A2 | 10/2004 |
| WO | WO2004049982 B1 | 12/2004 |
| WO | WO2005037152 A1 | 4/2005 |
| WO | WO2005058415 A1 | 6/2005 |
| WO | WO2005060869 A2 | 7/2005 |
| WO | WO2005060882 A1 | 7/2005 |
| WO | WO2005065412 A2 | 7/2005 |
| WO | WO2005097012 A2 | 10/2005 |
| WO | WO2005099591 A2 | 10/2005 |
| WO | WO2005110244 A1 | 11/2005 |
| WO | WO2005110280 A2 | 11/2005 |
| WO | WO2005112822 A1 | 12/2005 |
| WO | WO2005120363 A1 | 12/2005 |
| WO | WO2006014496 A2 | 2/2006 |
| WO | WO2006016894 A1 | 2/2006 |
| WO | WO2006020370 A2 | 2/2006 |
| WO | WO2006028898 A2 | 3/2006 |
| WO | WO2006034062 A1 | 3/2006 |
| WO | WO2006060049 A2 | 6/2006 |
| WO | WO2006062996 A2 | 6/2006 |
| WO | WO2006078781 A1 | 7/2006 |
| WO | WO2006078927 A1 | 7/2006 |
| WO | WO2006102012 A1 | 9/2006 |
| WO | WO2006102240 A2 | 9/2006 |
| WO | WO2006124880 A2 | 11/2006 |
| WO | WO2006127593 A2 | 11/2006 |
| WO | WO2006133311 A2 | 12/2006 |
| WO | WO2007019117 A1 | 2/2007 |
| WO | WO2007030829 A2 | 3/2007 |
| WO | WO2007038715 A1 | 4/2007 |
| WO | WO2007041598 A1 | 4/2007 |
| WO | WO2007075396 A2 | 7/2007 |
| WO | WO2007092390 A2 | 8/2007 |
| WO | WO2007107990 A2 | 9/2007 |
| WO | WO2007127209 A2 | 11/2007 |
| WO | WO2007136468 A2 | 11/2007 |
| WO | WO2007139920 A2 | 12/2007 |
| WO | WO2007142829 A1 | 12/2007 |
| WO | WO2007142832 A1 | 12/2007 |
| WO | WO2007142833 A1 | 12/2007 |
| WO | WO2007142834 A1 | 12/2007 |
| WO | WO2007145684 A2 | 12/2007 |
| WO | WO2008005510 A2 | 1/2008 |
| WO | WO2008030403 A1 | 3/2008 |
| WO | WO2008033409 A1 | 3/2008 |
| WO | WO2008033474 A2 | 3/2008 |
| WO | WO2008039800 A2 | 4/2008 |
| WO | WO2008101048 A2 | 8/2008 |
| WO | WO2008106041 A1 | 9/2008 |
| WO | WO2008106279 A1 | 9/2008 |
| WO | WO2008112942 A2 | 9/2008 |
| WO | WO2008127552 A2 | 10/2008 |
| WO | WO2008141288 A1 | 11/2008 |
| WO | WO2008148047 A2 | 12/2008 |
| WO | WO2008150905 A1 | 12/2008 |
| WO | WO2008154450 A1 | 12/2008 |
| WO | WO2008154594 A2 | 12/2008 |
| WO | WO2009011881 A1 | 1/2009 |

(56) References Cited

FOREIGN PATENT DOCUMENTS

| WO | WO2009011882 A2 | 1/2009 |
|---|---|---|
| WO | WO2009012335 A1 | 1/2009 |
| WO | WO2009036244 A1 | 3/2009 |
| WO | WO2009046126 A1 | 4/2009 |
| WO | WO2009082710 A1 | 7/2009 |
| WO | WO2009085107 A1 | 7/2009 |
| WO | WO2009086549 A1 | 7/2009 |
| WO | WO2009097582 A1 | 8/2009 |
| WO | WO2009097585 A1 | 8/2009 |
| WO | WO2010115011 A1 | 10/2010 |
| WO | WO2011062882 A1 | 5/2011 |
| WO | WO2011073970 A1 | 6/2011 |
| WO | WO2011099940 A8 | 8/2011 |
| WO | WO2012103531 A2 | 8/2012 |
| WO | 2014113483 A1 | 7/2014 |
| WO | 2015138465 A1 | 9/2015 |

OTHER PUBLICATIONS

Probiotics may improve results after weight loss surgery (http://www.malleysurgical.com/blog/85probioticsmayimproveresultsafterweightloss, published Oct. 29, 2012, accessed Feb. 10, 2017).*
Buchwald, Henry et al., "Bariatric Surgery: A Systematic Review and Meta-Analysis", JAMA, Oct. 13, 2004, 292 (14), pp. 1724-1737.
Cummings, David E. et al., "Role of the bypassed proximal intestine in the anti-diabetic effects of bariatric surgery", Surgery for Obesity and Related Diseases 3 2007, pp. 109-115.
Daniels, Stephen, "Probiotics may 'counter obesity and diabetes': NIH study", Jul. 10, 2013, downloaded from http://www.nutraingredients-usa.com/research/probiotics-may-counter-obesity-and-diabetes-NIH-study, 2 pages.
International Search Report and Written Opinion issued in PCT/US12/58202, dated Jan. 23, 2013, 14 pages.
International Search Report and Written Opinion issued in PCT/US2010/029648, dated Aug. 24, 2010.
International Search Report and Written Opinion issued in PCT/US2010/041574, dated Jan. 25, 2011.
International Search Report and Written Opinion issued in PCT/US2011/020560, dated Mar. 28, 2011, 10 pages.
International Search Report and Written Opinion issued in PCT/US2011/061193.
International Search Report and Written Opinion issued in PCT/US2012/023048, dated Jun. 22, 2012.
International Search Report and Written Opinion issued in PCT/US2014/011702, dated Mar. 21, 2014, 9 pages.
Invitation to Pay Additional Fees issued in PCT/US2010/029648, dated Jun. 1, 2010.
Ley, Ruth E. et al., "Microbial ecology: human gut microbes associated with obesity", Nature, vol. 44, No. 7122, pp. 1022-1023, 2006.
Pories, Walter J. et al., "Surgical Treatment of Obesity and its Effect on Diabetes: 10-6 Follow-up", Am J Clin Nutr 1992, 55, 582S-585S.
Pories, Walter J. et al., "Who Would Have Thought It? An Operation Proves to be the Most Effective Therapy for Adult-Onset Diabetes Mellitus", Annals of Surgery, Sep. 1995, 222(3), pp. 339-352.
Rodriguez-Grunert, Leonardo et al., "First Human Experience With endoscopically Delivered and retrieved duodenal-jejunal bypass sleeve", Surgery for Obesity and Related diseases 4 (2008) 55-59.
Rubino, Francesco et al,, "Effect of Duodenal-Jejunal Exclusion in a Non-Obese Animal Model of Type 2 Diabetes", Annals of Surgery, vol. 239, No. 1, Jan. 2004, pp. 1-11.
Rubino, Francesco et al., "Potential of Surgery for Curing Type 2 Diabetes Mellitus", Annals of Surgery, Nov. 2002, 236(5), 554-559.
Rubino, Francesco et al., "The Mechanism of Diabetes Control After Gastrointestinal Bypass Surgery Reveals a Role of the Proximal Small Intestine in the pathophysiology of Type 2 Diabetes", Annals of Surgery, 244(5), Nov. 2006, pp. 741-749.
Schouten, Ruben et al., "A Multicenter, Randomized Efficacy Study of the endoBarrier Gastrointestinal Liner for Presurgical Weight Loss Prior to Bariatric Surgery", Annals of Surgery, vol. 251, No. 2, Feb. 2010, pp. 236-243.
Strader, Apr. et al., "Weight Loss Through Ileal transposition is accompanied by increased ileal hormone secretion and synthesis in rats", Am J Physiol Endocrinol Metab 288: E447-E453, 2005.
Troy, Stephanie et al., "Intestinal Gluconeogenesis is a key factor for early metabolic changes after gastric bypass but not after gastric lap-band in mice", Cell metabolism 8, 201-211, Sep. 3, 2008.
Vetter, Marion et al., "Narrative Review: Effect of bariatric Surgery on Type 2 Diabetes Mellitus", Annals of Internal Medicine, Jan. 20, 2009, 150(2), pp. 94-104.
Yadav, Hariom et al., Beneficial Metabolic Effects of a Probiotic via Butyrate-induced GLP-1 Hormone Secretion, Journal of Biological Chemistry, 2013, vol. 288, pp. 25088-25097.
International Preliminary Report on Patentability issued in PCT/US2014/011702, dated Jul. 30, 2015, 7 pages.
International Search Report and Written Opinion issued in PCT/US2015/019730, dated Mar. 10, 2015, 15 pages.
Partial European Search Report issued in EP14172564, dated Feb. 12, 2015 , 7 pages.
International Search Report and Written Opinion issued in PCT/US2017/020494, dated Apr. 3, 2017, 10 pages.
Parnell, Jill A., et al. "Prebiotic Fiber Modulation of the Gut Microbiota Improves Risk Factors for Obesity and the Metabolic Syndrome." Gut Microbes, 3(1):29-34, Jan. 1, 2012.
Preliminary Report on Patentability issued in PCT/US2015/019730 dated Sep. 22, 2016, 7 pages.
Supplemental European Search Report issued in EP Application 14740554 dated Sep. 2016, 7 pages.
Woodard et al., Probiotics Improve Outcomes After Roux-en-Y Gastric Bypass Surgery: A Prospective Randomized Trial, J Gastrointest Surg (2009) 13:1198-1204.

* cited by examiner

SYSTEM AND METHOD FOR AFFECTING INTESTINAL MICROBIAL FLORA

CROSS-REFERENCE TO RELATED APPLICATIONS

This application claims priority to Provisional Application No. 61/752,839, filed Jan. 15, 2013, which is herein incorporated by reference in its entirety. This application is related to the following commonly assigned applications and patents, each of which is incorporated herein by reference: (1) U.S. Pat. No. 8,211,186; (2) U.S. Pat. No. 8,282,598; (3) U.S. Patent Application Publication 2011/0106273, published May 5, 2011; (4) U.S. Patent Application Publication 2012/0065571, published Mar. 15, 2012; (5) U.S. Patent Application Publication 2012/0184893, published Jul. 19, 2012; (6) U.S. Patent Application Publication 2013/0030351, published Jan. 31, 2013; and (7) U.S. Patent Application Publication 2012/0302936, published Nov. 29, 2012.

TECHNICAL FIELD

This invention relates to implants that are placed within gastrointestinal organs including in the distal portion of the stomach and the small intestine. In particular, it relates to an implant system and method that can be placed by endoscopic means, in order to reduce colonization of the intestines by certain bacteria and treat chronic diseases.

BACKGROUND

Recent clinical evidence suggests that surgical treatments for obesity, such as Rouen-Y gastric bypass (RYGB) can cause remission of diabetes in 75%-80% of patients. Hence, minimally invasive procedures including intra-luminal gastrointestinal bypass implants have recently been proposed to mimic all or some of the anatomical, physiological and metabolic changes achieved by a Rouen-Y gastric bypass. Some of these procedures provide a means to internally bypass a portion of the small intestine. It has been observed through anecdotal clinical evidence that the effect of such bypass means may be causing remission of metabolic disorders, which persists months after the bypass means is removed from a patient.

Current pharmaceutical approaches to modifying intestinal microbial flora involve the administration of therapy to selectively ameliorate "bad" (having a negative effect on the health of a patient) bacteria in the intestines in order to promote colonization by "good" (having a positive effect on the health of a patient) bacteria. The field of probiotic-based pharmaceutical therapy is based on such a paradigm. One of the shortcomings of such an approach is the difficulty in targeting just the bad bacteria, which has already colonized in the intestines, to be eliminated. Therefore, a need still exists for a system and a method for affecting the intestinal microbial flora to benefit a patient.

SUMMARY

Example 1 is a system for affecting intestinal microbial flora. The system comprises: an intestinal sleeve that is implanted in a patient and bypasses a section of the intestine; and probiotics, prebiotics or pharmacologic therapy used in combination with the intestinal sleeve.

Example 2 is the system of Example 1 further comprising an anchoring element, wherein the sleeve is anchored at a pyloric junction of a patient joining the stomach and the intestine by the anchoring element.

Example 3 is the system of Example 2 in which the anchoring element comprises two flanges, with one flange on an intestinal side and one flange on a stomach side.

Example 4 is the system of Example 2 in which the anchoring element is made from Nitinol.

Example 5 is the system of Example 2 in which the anchoring element further comprises a covering comprising a biocompatible polymer or fabric.

Example 6 is the system of Example 1 in which the sleeve is impregnated, coated or otherwise modified to include the probiotics, prebiotics or pharmacologic therapy.

Example 7 is a method of affecting intestinal microbial flora. The method comprises the steps of: implanting an intestinal sleeve in a patient that bypasses a section of the intestine; and administering probiotics, prebiotics or pharmacologic therapy to patient.

Example 8 is the method of Example 7 in which the sleeve is attached to an anchoring element that anchors the intestinal sleeve at a pyloric junction of the patient.

Example 9 is the method of Example 8 in which the anchoring element comprises two flanges, with one flange on an intestinal side and one flange on a stomach side.

Example 10 is the method of Example 8 in which the anchoring element further comprises a covering comprising a biocompatible polymer or fabric.

Example 11 is the method of Example 7 in which the sleeve is implanted in the patient for a finite period of time.

Example 12 is the method of Example 7 in which the probiotics, prebiotics or pharmacologic therapy is administered to the patient starting a few days before the sleeve is implanted.

Example 13 is the method of Example 7 in which the probiotics, prebiotics or pharmacologic therapy is administered to the patient when the sleeve is implanted.

Example 14 is the method of Example 7, further comprising the step of removing the sleeve from the patient.

Example 15 is the method of Example 14 in which the probiotics, prebiotics or pharmacologic therapy is administered to the patient starting a few days prior to removing the sleeve.

Example 16 is the method of Example 14 in which the probiotics, prebiotics or pharmacologic therapy is administered to the patient starting on the day the sleeve is removed.

Example 17 is the method of Example 7 in which the sleeve is implanted endoscopically.

Example 18 is the method of Example 14 in which the sleeve is removed endoscopically.

Example 19 is a method of affecting intestinal microbial flora in a patient. The method comprises the steps of: implanting a sleeve in the patient's intestine that bypasses a section of the intestine; and removing the sleeve after a period of time and after intestinal microbial flora has been affected.

Example 20 is the method of Example 19 in which the sleeve is impregnated, coated or otherwise modified to include probiotics, prebiotics or pharmacologic therapy.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

The present invention involves an alternative or adjunct to probiotic therapy or other pharmacologic therapy to establish a new, more beneficial milieu of intestinal microbial flora. The result of good bacteria being more prevalent than bad bacteria in the intestine may resolve various ailments thought to be caused by the prevalence of bad bacteria over good. The present invention involves placing a sleeve within the intestine (i.e., gut) for a finite period of time to eradicate the colonization of the intestine by bacteria that play a role in metabolic disorders such as diabetes, obesity or general malaise (bad bacteria). In particular, an implant system may be used that can be placed by endoscopic means, anchored at the pyloric junction and connected to a sleeve component that extends into the jejunum. Placing the sleeve within a specific portion of the intestine can effectively starve the gut microbes of nutrients, reducing or altogether eliminating the bad gut microbes. The patient can then be administered probiotic therapy or other pharmacologic therapy while the implant is in place or after it has been removed to establish a healthier colony of bacteria in the intestine, thereby resolving various ailments. Also, alternatively, the sleeve itself could be used to deliver probiotic therapy while in place. This may include impregnating or coating the sleeve with probiotics or otherwise modifying the sleeve to carry such materials to a desired location within the anatomy.

The sleeve or implant system that may be used in the present invention may be of any suitable type. Exemplary embodiments of such an implant system or sleeve are depicted in the application, but other suitable devices or systems are also contemplated. Some particular exemplary devices or systems are included in a patent and a patent application assigned to the same assignee as the present invention, which are U.S. Pat. No. 8,211,186; and US Publication No. 2012/0253259, and are herein incorporated by reference.

Figure 1:
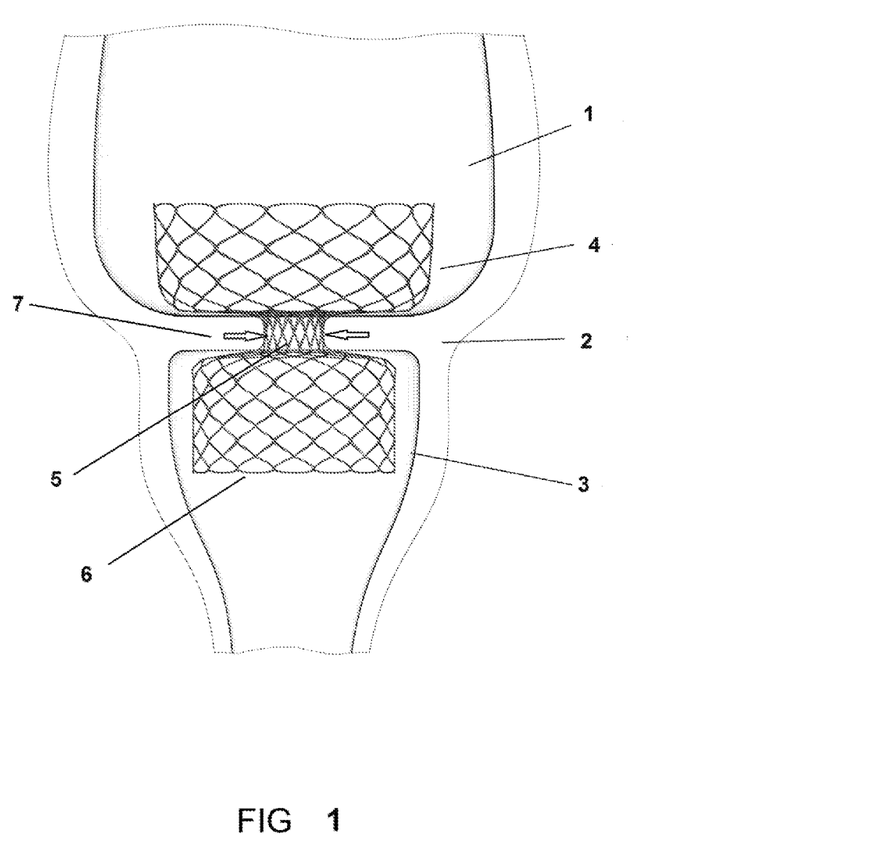
FIG. 1 shows an enlarged view of the gastrointestinal anatomy at the junction between the stomach and the duodenum, including an anchoring element.

FIG. 1 shows an enlarged view of the gastrointestinal anatomy at the junction between the stomach and the duodenum, including the pyloric antrum 1, the pylorus 2, and the duodenal bulb 3. A soft, braided or laser-cut anchoring element 4 is placed at the pyloric junction (i.e., extending across the pylorus). The anchoring element may be made from Nitinol. The anchoring element 4 may be one component of an implant system that includes a sleeve that extends into the duodenum. As shown, the anchoring element 4 is shaped such that it does not exert radial forces on the stomach wall or the duodenal wall for anchoring when the pyloric junction (the pyloric canal and the sphincter) is in a relaxed state. It is retained within the pyloric junction due to its shape, which has an outer diameter larger than the maximum outer diameter of the pyloric orifice. The anchoring element 4 includes a proximal portion (i.e., the portion located in the pyloric antrum 1), a distal portion 6 (i.e., the portion located in the duodenal bulb 3, and a neck portion 5 adapted to extend through the pylorus 2. Additionally, during normal physiologic function of the pylorus 2, the tissue may exert a closing force 7 on the neck portion of the implant 5. In this case, the neck portion of the implant will compress and not inhibit normal function of the body. According to various embodiments, the proximal 4 and distal portion 6 of the implant are shaped such that each has an unconstrained diameter of between about 15 and about 35 millimeters, and the neck portion 5 has an unconstrained diameter of between about 5 and about 15 millimeters.

Figure 2:
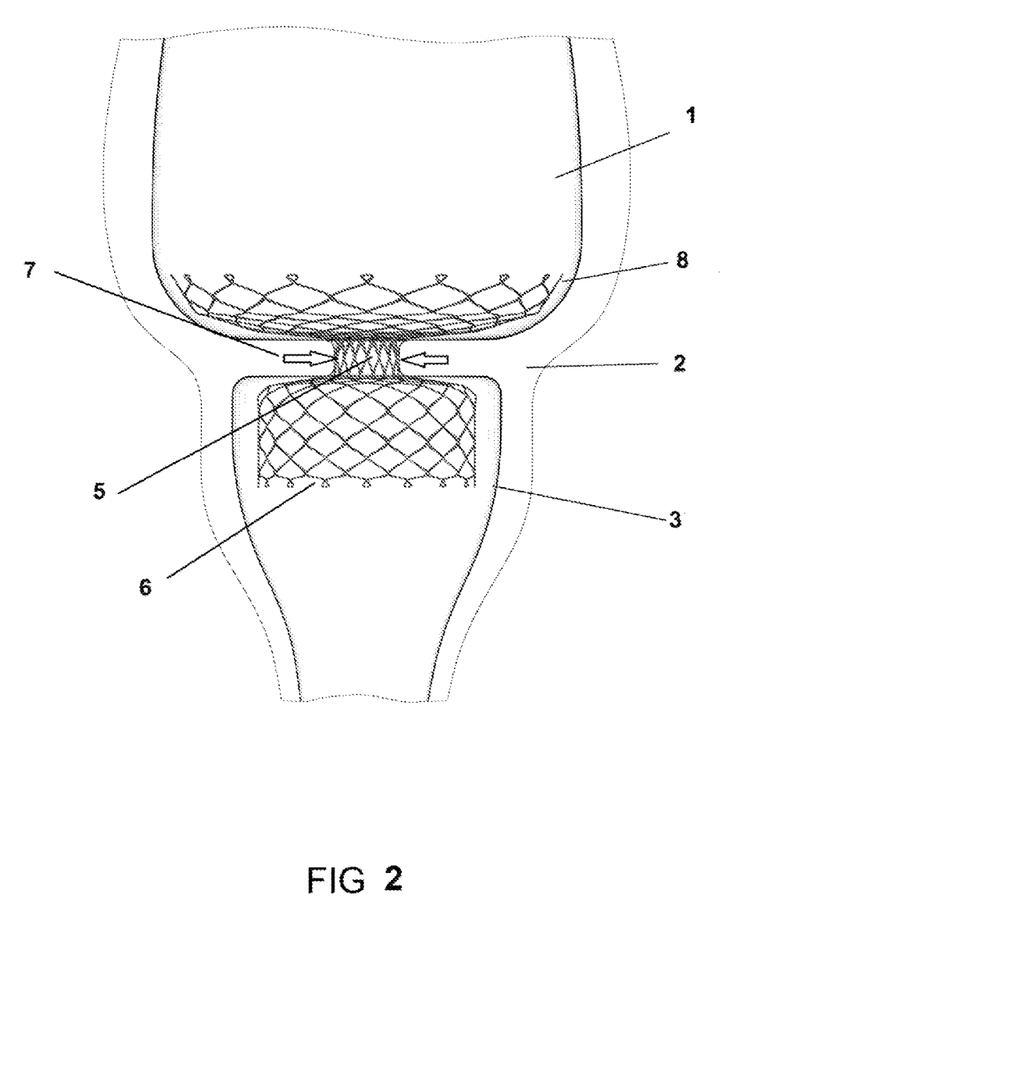
FIG. 2 shows another anchoring element having an alternate shape.

FIG. 2 shows another anchoring element 8 having an alternate shape. In this instance, the proximal portion of the anchoring element 8 (i.e., the portion located on the pyloric antrum side) is more disk-like and serves as a pronounced anchoring/retaining flange for the device. In some embodiments, the proximal portion of the anchoring element 8 has a maximum or unconstrained diameter slightly larger than an internal diameter of the pyloric antrum 1, such that the element exerts a slight radial force on the wall of the pyloric antrum 1.

Figure 3:
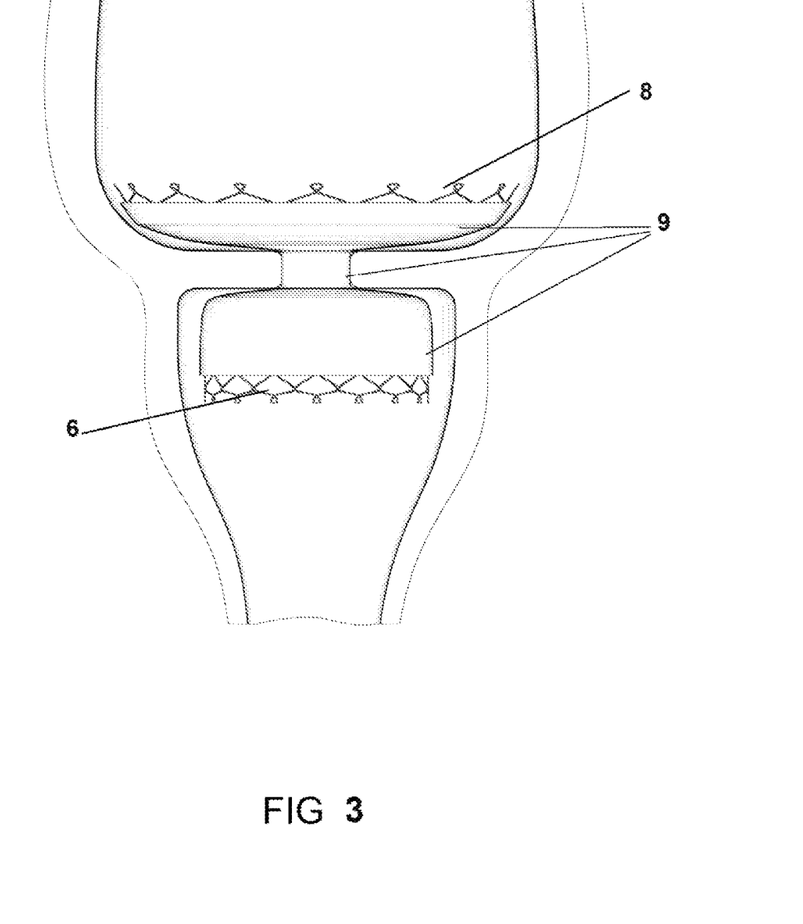
FIG. 3 shows an exemplary embodiment in which the anchoring element includes a cover.

In order to minimize or prevent abrasive injury to tissue and tissue in-growth, and to provide for ease of replacement, exemplary embodiments of the anchoring elements shown in FIGS. 1 and 2 could be covered. FIG. 3 shows an exemplary embodiment in which the anchoring element 8 includes a cover 9. The material comprising the cover 9 could be a flexible woven fabric or nonwoven, extruded polymeric material used in synthetic medical grafts such as polyurethane, silicone, expanded polytetrafluoroethylene (ePTFE), or may be dip coated with such materials. Other suitable materials are also contemplated.

Figure 4:
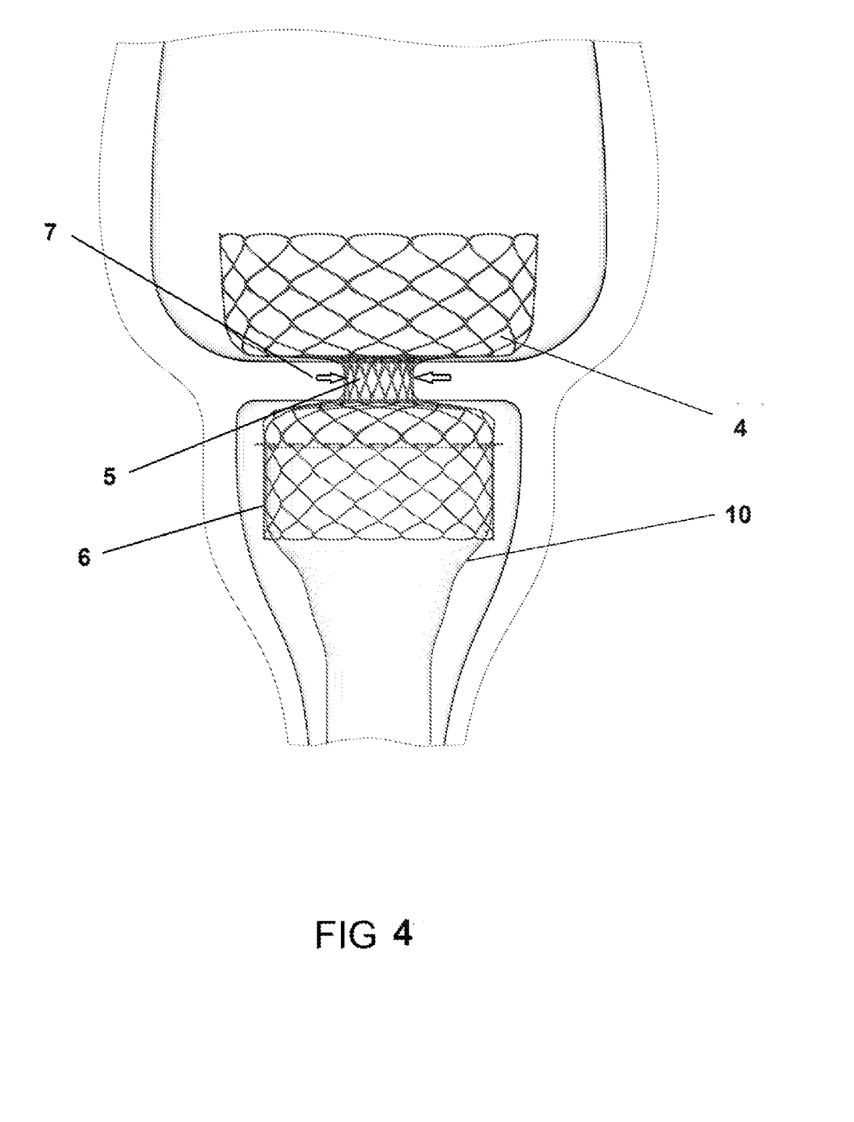
FIG. 4 shows the anchoring element of FIG. 1 with a thin sleeve attached for carrying food from the stomach to the distal small intestine.

FIG. 4 shows the anchoring element 4 of FIG. 1 with a thin sleeve 10 attached for carrying food from the stomach to the distal small intestine. The sleeve 10 is preferably constructed of an impermeable material that is resistant to both stomach acid and alkaline intestinal secretions. The sleeve 10 may be made from biocompatible materials such as fluoropolymers (e.g., fluorinated ethylene propylene (FEP), perfluoroalkoxy (PFA) and ePTFE), silicone and polyurethanes, or soft metallic fabric structures made out of metals such as stainless steel. The wall thickness of the sleeve 10 is preferably in the range of 0.001 inches (0.03 mm) to 0.010 inches (0.25 mm) and the diameter of the sleeve is selected to match the diameter of the small intestine of the patient, usually between 20 to 30 mm.

Figure 5:
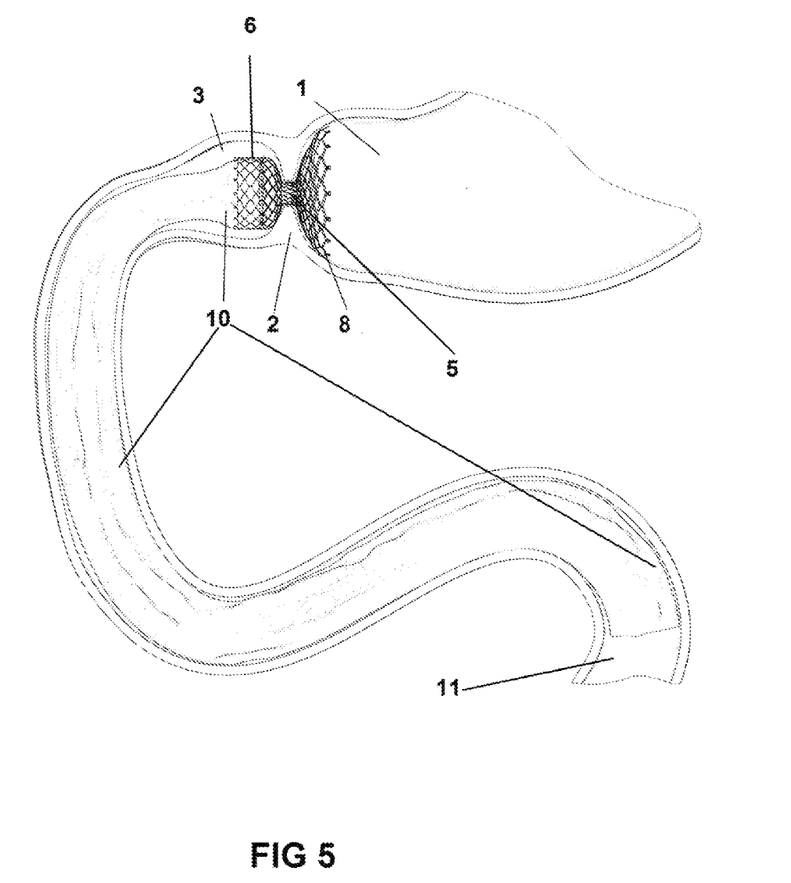
FIG. 5 shows the sleeve of FIG. 4 extending about 2 feet in length into the proximal jejunum.

FIG. 5 shows the sleeve 10 of FIG. 4 extending about 2 feet (0.61 m) in length into the proximal jejunum 11. The sleeve 10 prevents food from contacting the wall of the proximal intestine and delivers it directly to the distal portion of the small intestine. The isolation of nutrients from the wall of the small intestine can starve the gut microbes or bacteria of essential nutrients in that region and can lead to amelioration of at least a certain percentage of such bacteria.

Figure 6:
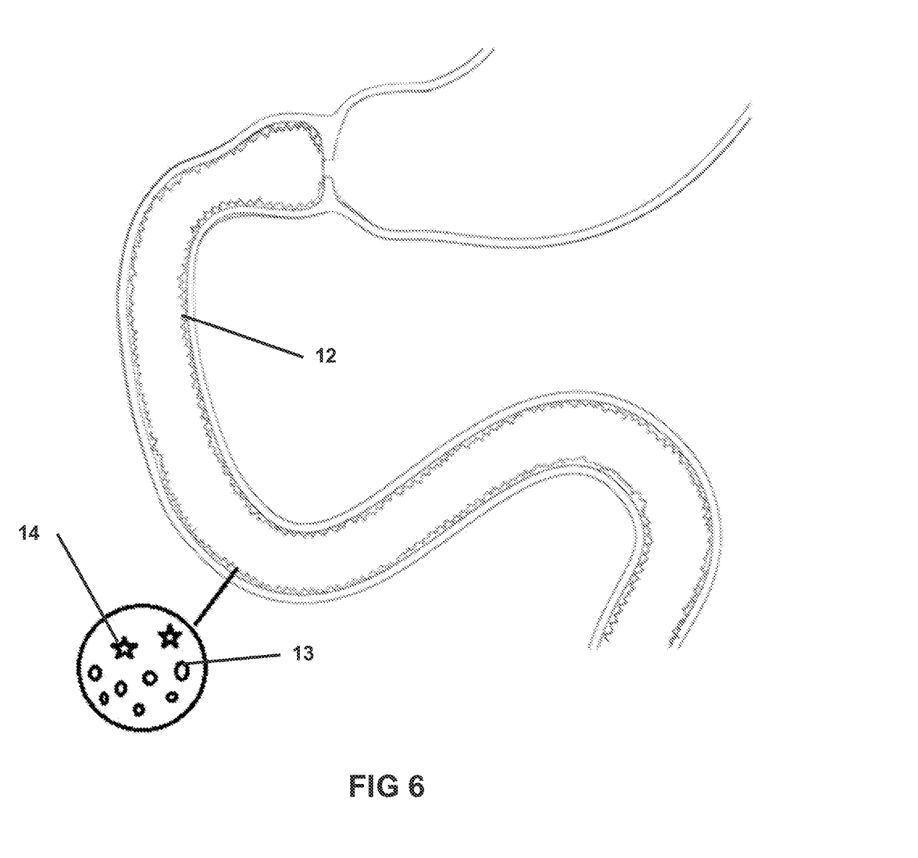
FIG. 6 shows a simplified illustration of a patient's intestine that is suffering from a chronic disease as a result of an unfavorable balance between bad bacteria (circles) over good bacteria (stars)

FIG. 6 shows a simplified illustration of a patient's intestine that is suffering from a chronic disease as a result of an unfavorable balance between bad bacteria (circles 13) over good bacteria (stars 14). The figure illustrates the problem that the therapeutic approach of this invention seeks to address. The illustration includes the same anatomy as shown in FIG. 5 prior to implantation of the sleeve 10.

In patients suffering from metabolic disorders such as type 2 diabetes and obesity, or autoimmune diseases such as rheumatoid arthritis and type 1 diabetes, the microbial flora lining the gut (or intestine) 12 is believed to be composed predominantly of bacteria that are not beneficial. For example, obese people are more likely to have a smaller proportion of *Bacteroides* (good bacteria) to Firmicutes (bad bacteria) within their guy. These bad bacteria 13 can effect nutrient absorption, signaling to the brain or participate in biochemical reactions that lead to chronic ailments. The type of bacterial colonies inhabiting a patient's gut might have origins in their diet, their environment and genetic factors. The present invention aims to change this microbial flora by initially eliminating a large portion of the bacteria by starving them of nutrition. Probiotic therapy may then be used to establish good microbial flora in the intestine.

Figure 7:
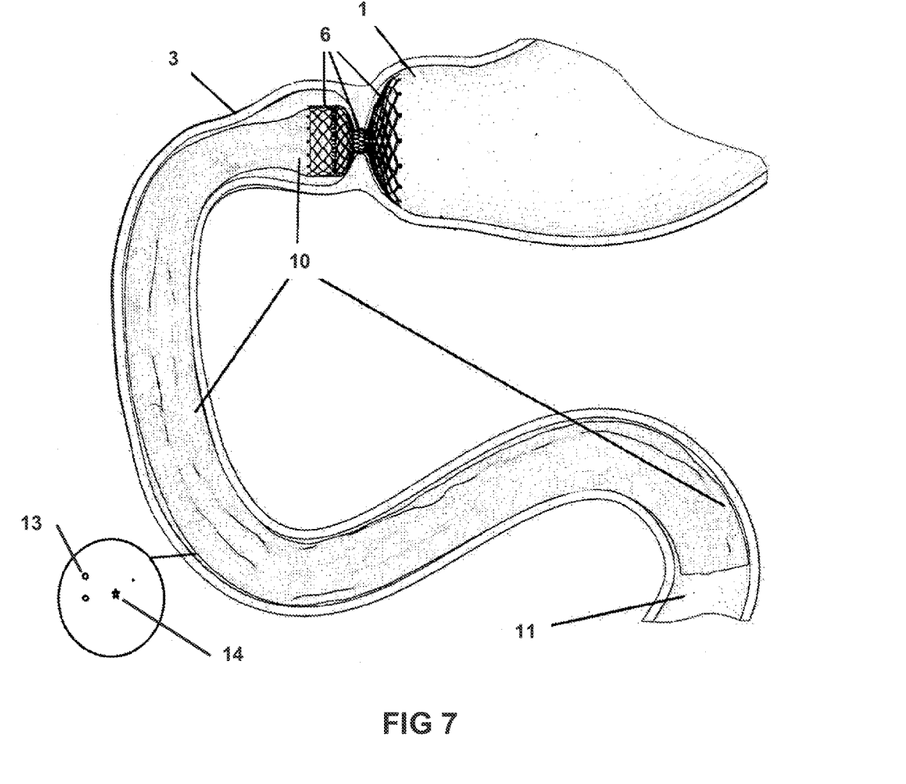
FIG. 7 shows the patient's intestine (from FIG. 6) a few days after implantation of the sleeve described in FIG. 5.

FIG. 7 shows the patient's intestine (from FIG. 6) a few days after implantation of the sleeve 10 described in FIG. 5. The effect of the sleeve 10 can already be seen as the composition of gut microbial flora has been modified. There is already a significant reduction in the number of bad bacteria 13 which may immediately result in remission of certain diseases. As an example, modification of the gut microbial flora after implantation of an intestinal sleeve in a patient with type 2 diabetes seems to cause normalization of glucose parameters within only a few days after the procedure. This modification also provides a foundation upon which the process of establishing new gut microbial flora can be started.

Figure 8:
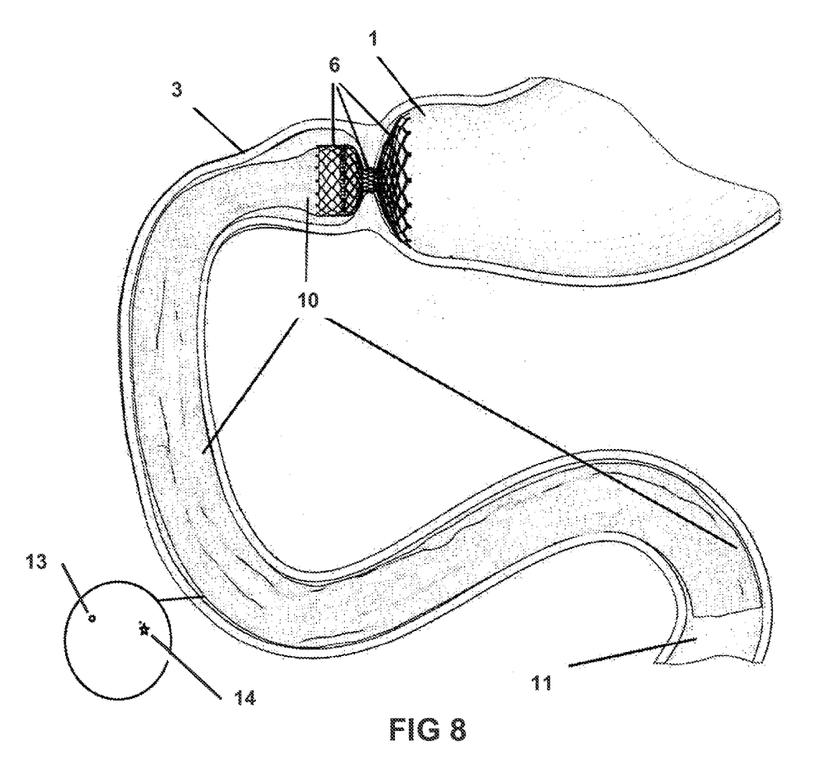
FIG. 8 shows the patient's intestine after a period of approximately weeks after FIG. 7, and just prior to explanation of the sleeve.

FIG. 8 shows the patient's intestine after a period of approximately weeks after FIG. 7, and just prior to explanation of the sleeve. The patient's anatomy has been further modified. The result is a significant reduction in the amount of bacteria in the gut. Here, the gut flora has been dramatically altered without the use of any antibiotics or pharmaceutical therapy, by simply preventing nutrients from reaching the gut microbes. This now provides a substrate for the repopulation of the gut with beneficial bacteria.

Figure 9:
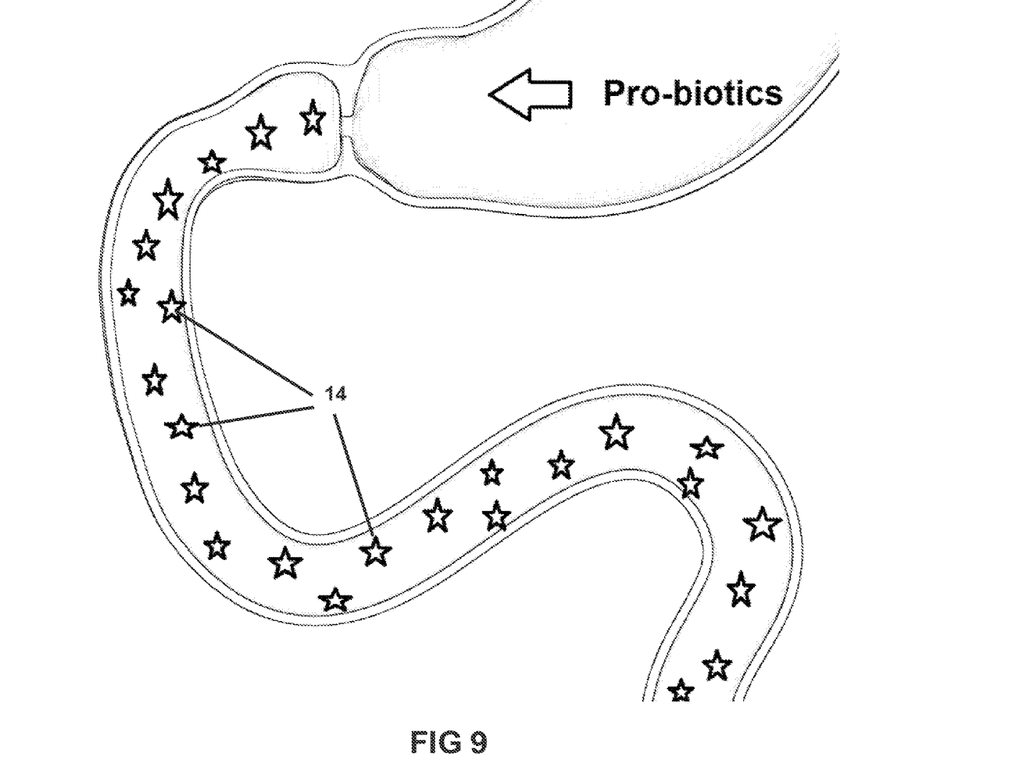
FIG. 9 shows the patient's intestine after the sleeve has been explanted and probiotic therapy is initiated.

FIG. 9 illustrates the patient's intestine after the sleeve has been explanted and probiotic therapy is initiated. The goal of this step is to deliver beneficial bacteria 14 to the intestine in order to establish a healthier colony of microbes within the area modified by the sleeve. This may be accomplished as the patient consumes healthy meals following rules of a probiotic diet, through oral supplements or through specially prepared foods.

Figure 10:
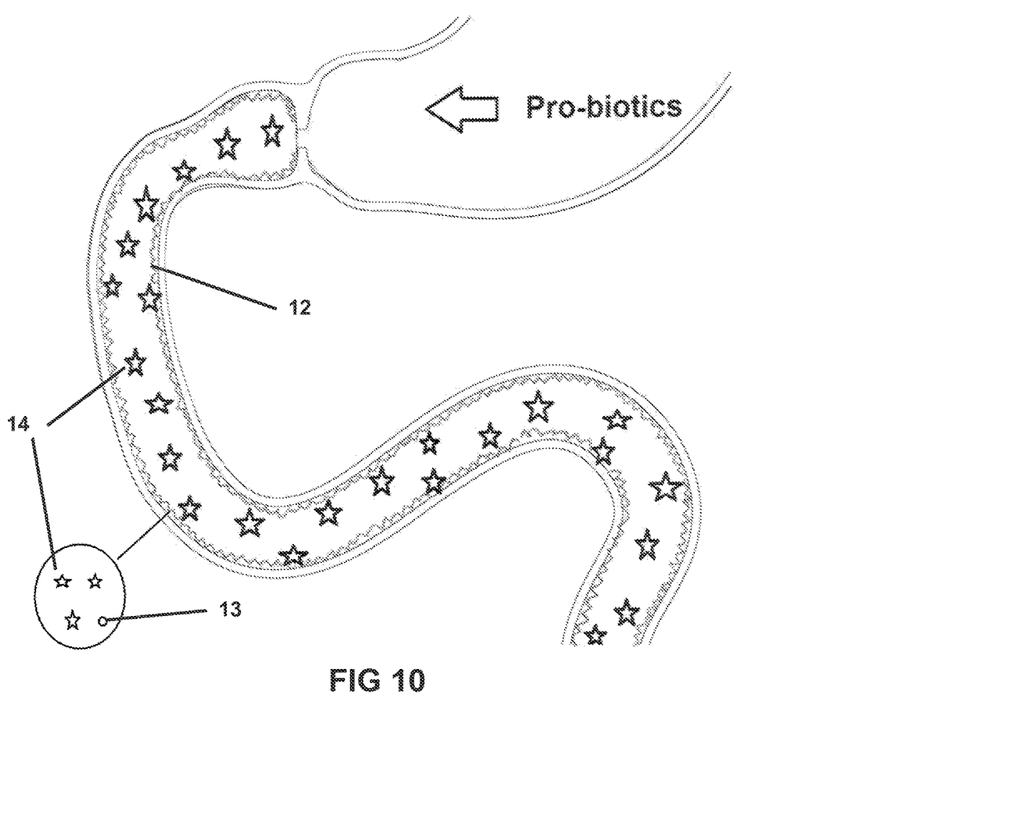
FIG. 10 shows an outcome of administering the probiotic therapy described in FIG. 9 for a period of several weeks.

FIG. 10 illustrates the outcome of administering the probiotic therapy described in FIG. 9 for a period of several weeks. At this point, the therapy has resulted in the establishment of new gut microbial flora 12 with a beneficial balance of more good bacteria 14 than bad 13.

Figure 11:
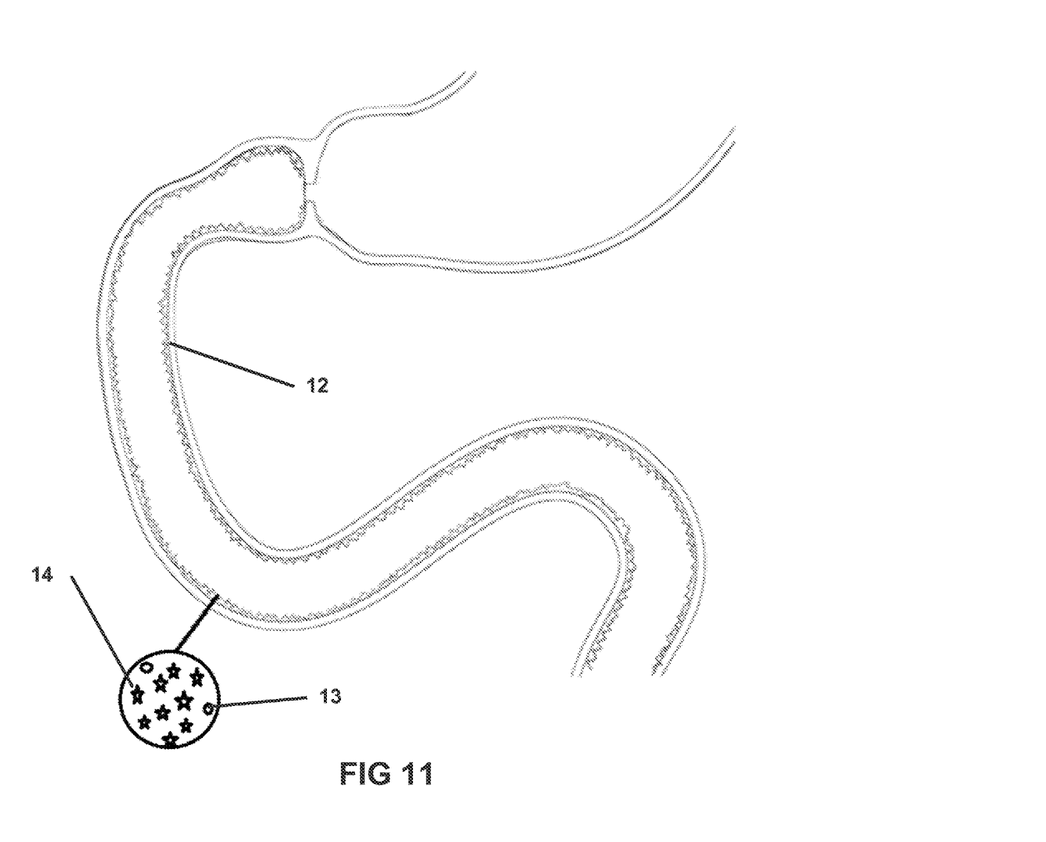
FIG. 11 shows a further continuation of the process described in FIG. 10 and a final outcome observed after the probiotic therapy is complete.

FIG. 11 illustrates a further continuation of the process described in FIG. 10 and the final outcome observed after the probiotic therapy is complete. Here the new healthy gut flora 12 has taken complete hold and is now composed of a greater percentage of good bacteria 14 than when the therapy was started. For the patient, the result will be remission of symptoms related to the original gut microbial imbalance, and possibly reversal of metabolic or autoimmune disorders such as obesity, diabetes or rheumatoid arthritis.

According to various embodiments of the invention, one or more of the systems described herein may be utilized to perform a therapeutic procedure including the following steps:

1. Implanting a thin intestinal sleeve that bypasses a specific section of the small intestine, in which the sleeve prevents nutrients from contacting the wall of the intestine and thereby helps to alter the microbial flora of that section of the intestine;

2. Removing the sleeve after a period of time. In various embodiments, the sleeve is removed after a period of three days. In other embodiments, the sleeve is removed anywhere from three days to three years after implantation; and 3. Administering probiotic or other pharmaceutical therapy to the patient to reestablish gut microbial flora that promotes health and helps reverse metabolic disorders, autoimmune diseases and other ailments, such therapy may be initiated before, right after implantation or upon explanation of the sleeve.

In 2006, researchers discovered that microbial populations in the gut are different between obese and lean people. The study, published in Nature (R. E. Ley, P. J. Turnbaugh, S. Klein, and J. I. Gordon, "Microbial ecology: human gut microbes associated with obesity," Nature, vol. 444, no. 7122, pp. 1022-1023, 2006), further demonstrated that when obese people lost weight, their microflora reverted back to that observed in a lean person. More recently, additional studies have shown that microbial populations can be prospectively altered to achieve a desired change in the gut microflora. For example, a recent study published in The Journal of Biological Chemistry (Yadav, H et. al, Beneficial Metabolic Effects of a Probiotic via Butyrate-induced GLP-1 Hormone Secretion. J. Biol. Chem. 2013 288: 25088-25097) showed that in animals, providing a probiotic dietary supplement containing a combination of eight bacterial strains; *Bifidobacterium breve, Bifidobacterium longum, Bifidobacterium infantis, Lactobacillus acidophilus, Lactobacillus plantarum, Lactobacillus paracasei, Lactobacillus bulgaricus*, and *Streptococcus thermophiles*; resulted in suppressed weight gain, lower blood glucose levels, and improved glucose and insulin tolerance compared to animals that did not receive the same therapy. The inventors recognized that the devices and methods disclosed herein could be effectively implemented to affect the microflora population in the intestines to capture the advantages set forth in these articles.

According to various embodiments of the present invention, any of the probiotics disclosed above may be used to complete the step of administering probiotics.

Other embodiments of the invention include the use of prebiotics in combination with an intestinal sleeve. Prebiotics, like probiotics, can play an important role in helping to colonize the gut with beneficial bacteria. Prebiotics are non-digestible food ingredients that function to stimulate the growth of bacteria in the digestive system. In the present invention, prebiotics could be administered in the same manner as described for probiotics, which is before, during and/or after sleeve implantation.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The invention claimed is:

1. A system for treating obesity and diabetes, the system comprising:
 a removable intestinal sleeve configured to be implanted along a treatment length of an intestine of a patient to prevent nutrients from contacting a lining of the intestine along the treatment length, such that an initial microbial population along the treatment length of the patient's intestine is reduced without the use of antibiotics, wherein the intestinal sleeve is impregnated or coated with a probiotic therapy such that the probiotic therapy is deliverable at least to the treatment length of the intestine of the patient to promote beneficial intestinal microbial flora at least along the treatment length of the intestine of the patient while the intestinal sleeve is implanted and after the intestinal sleeve is removed.

2. The system of claim 1, further comprising an anchoring element attached to the sleeve, wherein the sleeve is configured to be anchored at a pyloric junction of a patient by the anchoring element.

3. The system of claim 2, wherein the anchoring element comprises two flanges, with one flange configured to be located on an intestinal side and one flange configured to be located on a stomach side of a patient when implanted.

4. The system of claim 2, wherein the anchoring element is made from Nitinol.

5. The system of claim 2, wherein the anchoring element further comprises a covering comprising a biocompatible polymer or fabric.

* * * * *